US012802808B2

(12) United States Patent
Kandasamy et al.

(10) Patent No.: US 12,802,808 B2
(45) Date of Patent: Nov. 17, 2026

(54) METHODS AND SYSTEMS FOR VENTILATORS

(71) Applicant: GE Precision Healthcare LLC, Milwaukee, WI (US)

(72) Inventors: Srinivas Kandasamy, Bengaluru (IN); Manthram Sivasubramaniam, Bengaluru (IN); Sanketh Bhat, Bengaluru (IN); Etika Agarwal, Bengaluru (IN); Upasana Ramakrishnan, Bengaluru (IN)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 1088 days.

(21) Appl. No.: 17/456,351

(22) Filed: Nov. 23, 2021

(65) Prior Publication Data

US 2023/0162850 A1 May 25, 2023

(51) Int. Cl.

| | |
|---|---|
| ***G16H 40/60*** | (2018.01) |
| ***A61M 16/00*** | (2006.01) |
| ***G16H 40/63*** | (2018.01) |

(52) U.S. Cl.

CPC .......... *G16H 40/63* (2018.01); *A61M 16/024* (2017.08); *A61M 2205/3553* (2013.01)

(58) Field of Classification Search

CPC ........ G16H 40/40; G16H 40/63; G16H 50/50; G16H 20/40; A61M 16/024; A61M 2205/3553; A61M 16/0003; A61M 16/026; A61M 16/1005; A61M 2016/0027; A61M 2016/0033; A61M 2016/102; A61M 2016/1025; A61M 2205/15; A61M 2205/3327; A61M 2205/3331; A61M 2205/3379; A61M 2205/50; A61M 2205/502; A61M 2205/70; A61M 2205/702

See application file for complete search history.

(56) References Cited

U.S. PATENT DOCUMENTS

| | | | | |
|---|---|---|---|---|
| 7,395,216 | B2 | 7/2008 | Rosenfeld et al. | |
| 8,794,234 | B2 | 8/2014 | Jafari et al. | |
| 2008/0295837 | A1* | 12/2008 | McCormick | A61M 16/0051 600/529 |
| 2015/0165140 | A1* | 6/2015 | Cappelli | G01L 27/007 |
| 2018/0193578 | A1 | 7/2018 | Glenn et al. | |
| 2018/0221608 | A1 | 8/2018 | Schwaibold | |
| 2018/0317808 | A1 | 11/2018 | Wang et al. | |
| 2019/0046056 | A1* | 2/2019 | Khachaturian | A61B 5/0816 |
| 2020/0053086 | A1* | 2/2020 | Schwaibold | H04L 63/04 |
| 2022/0076822 | A1* | 3/2022 | Liu | G16H 40/67 |
| 2022/0148701 | A1* | 5/2022 | Cipollone | G16H 40/67 |

(Continued)

FOREIGN PATENT DOCUMENTS

| | | | |
|---|---|---|---|
| EP | 2259821 | B1 | 5/2012 |
| WO | 2011106246 | A1 | 9/2011 |

*Primary Examiner* — Timothy A Stanis
*Assistant Examiner* — Matthew R Moon
(74) *Attorney, Agent, or Firm* — McCoy Russell LLP

(57) ABSTRACT

Systems and methods are provided herein for analysis of performance of a mechanical ventilator. In one example, a method includes predicting a reliability of a ventilator during ventilator operation based on a discrepancy between a modeled ventilator parameter and a sensed ventilator parameter tracked over time, and further based on ventilator utilization.

6 Claims, 6 Drawing Sheets

(56) References Cited

U.S. PATENT DOCUMENTS

| | | | | |
|---|---|---|---|---|
| 2022/0160976 | A1* | 5/2022 | Zorzi de Miranda | A61M 16/0003 |
| 2022/0323711 | A1* | 10/2022 | Sanson | A61M 16/204 |
| 2023/0191063 | A1* | 6/2023 | Fox | A61M 16/0069 128/206.24 |

* cited by examiner

METHODS AND SYSTEMS FOR VENTILATORS

FIELD

Embodiments of the subject matter disclosed herein relate to analysis of ventilator performance, and more particularly to ventilator component reliability, including sensors and actuators.

BACKGROUND

Some types of medical equipment, such as incubators and anesthesia machines, may include an advanced breathing system for moving breathable air into and out of a patient's lungs. The advanced breathing system may include a device for monitoring an air flow rate of the patient's breath. In some examples, the device may include a flexible reed that is perpendicular to the air flow path that is sensitive to changes in air flow through the device. For example, the flexible reed may bend bidirectionally, such as in a first direction during inhalation and a second, opposite direction during exhalation, in proportion to a mass flow rate of each breath. The device may include two pressure ports, one on each side of the flexible reed, to determine a pressure differential across the reed. This pressure differential may be used to determine the mass flow rate of the breath.

Ventilators supplying air ventilation for patients without an ability to self-respire are common necessities for patients in intensive care units (ICU). In critical care environments, patient comfort may depend on performance and/or consistency of components in an architecture of ventilator systems, such as sensors and actuators, where a decrease in performance and/or consistency, even for a few seconds, may lead to patient discomfort. In one example, an oxygen sensor in a ventilator may be prone to variations in humidity during movement of a patient bed between an ICU and a surgical ward, which may result in increasing bias of the oxygen sensor due to a frequent change in humidity levels. Ventilators may operate in less controlled environments, where variations in humidity may be frequent. Redundant sensors may be present in some more advanced ventilators, increasing an accuracy of ventilator components at a higher manufacturing cost.

BRIEF DESCRIPTION

In one embodiment, a method for a ventilator comprises: predicting a reliability of a ventilator during ventilator operation based on a discrepancy between a modeled ventilator parameter and a sensed ventilator parameter tracked over time and ventilator utilization.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
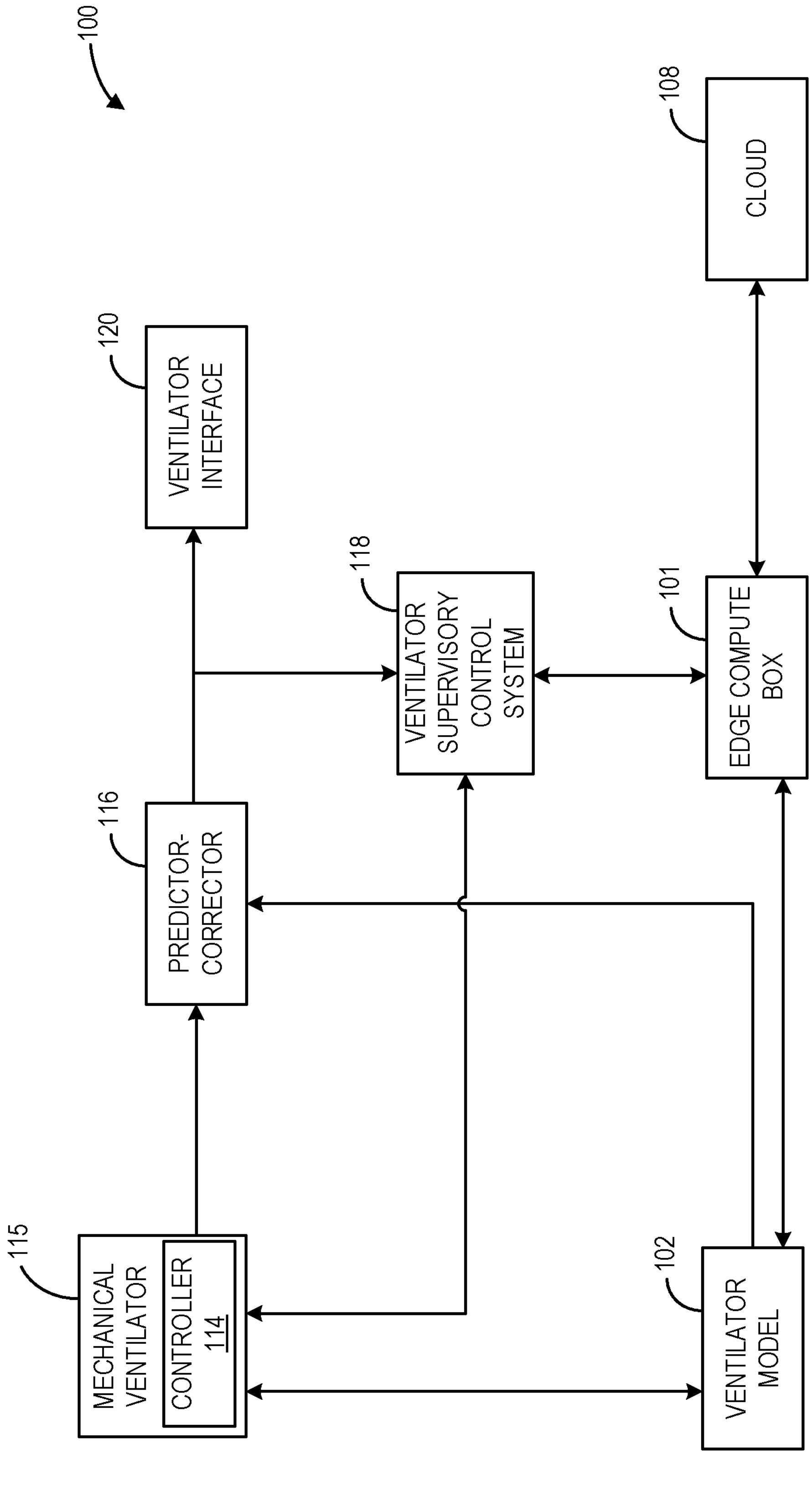
FIG. 1 illustrates a system for a mechanical ventilator.
Figure 2:
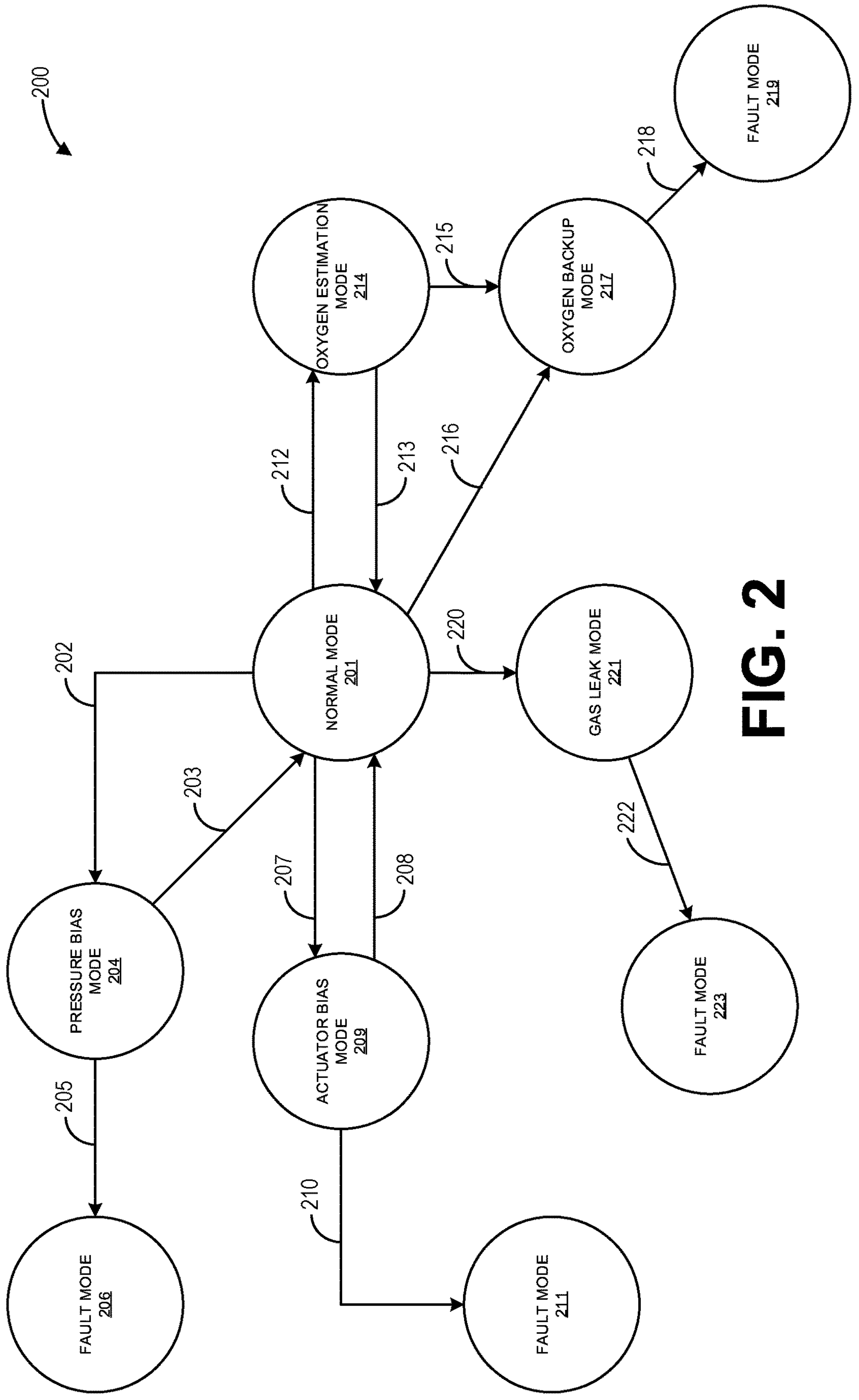
FIG. 2 illustrates a state machine based on a ventilator model and one or more sensor signals, where transitions from a first state to a second state may be based on a predicted reliability of the ventilator.
Figure 4:
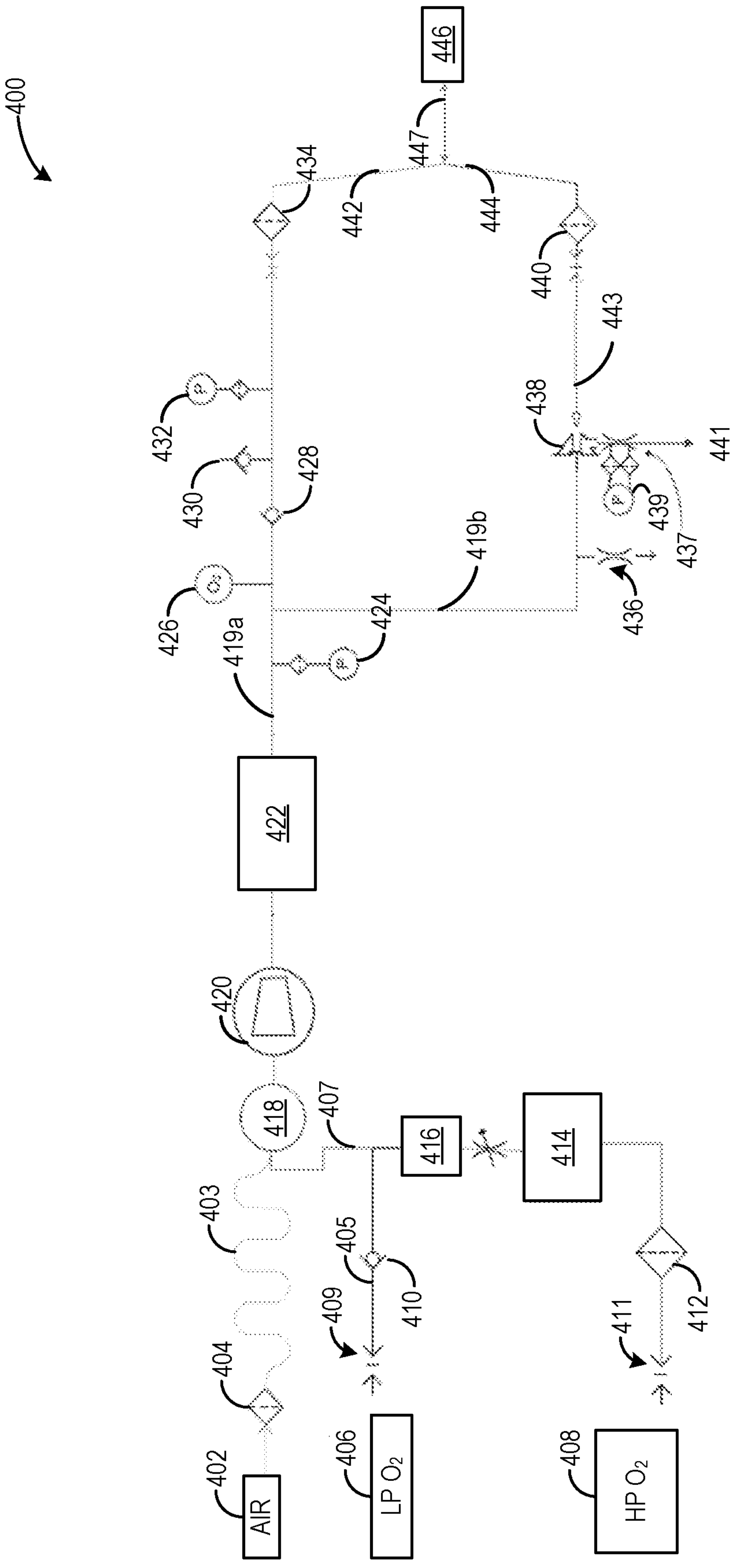
FIG. 4 illustrates a schematic diagram of an existing ventilator system pneumatic architecture.
Figure 5:
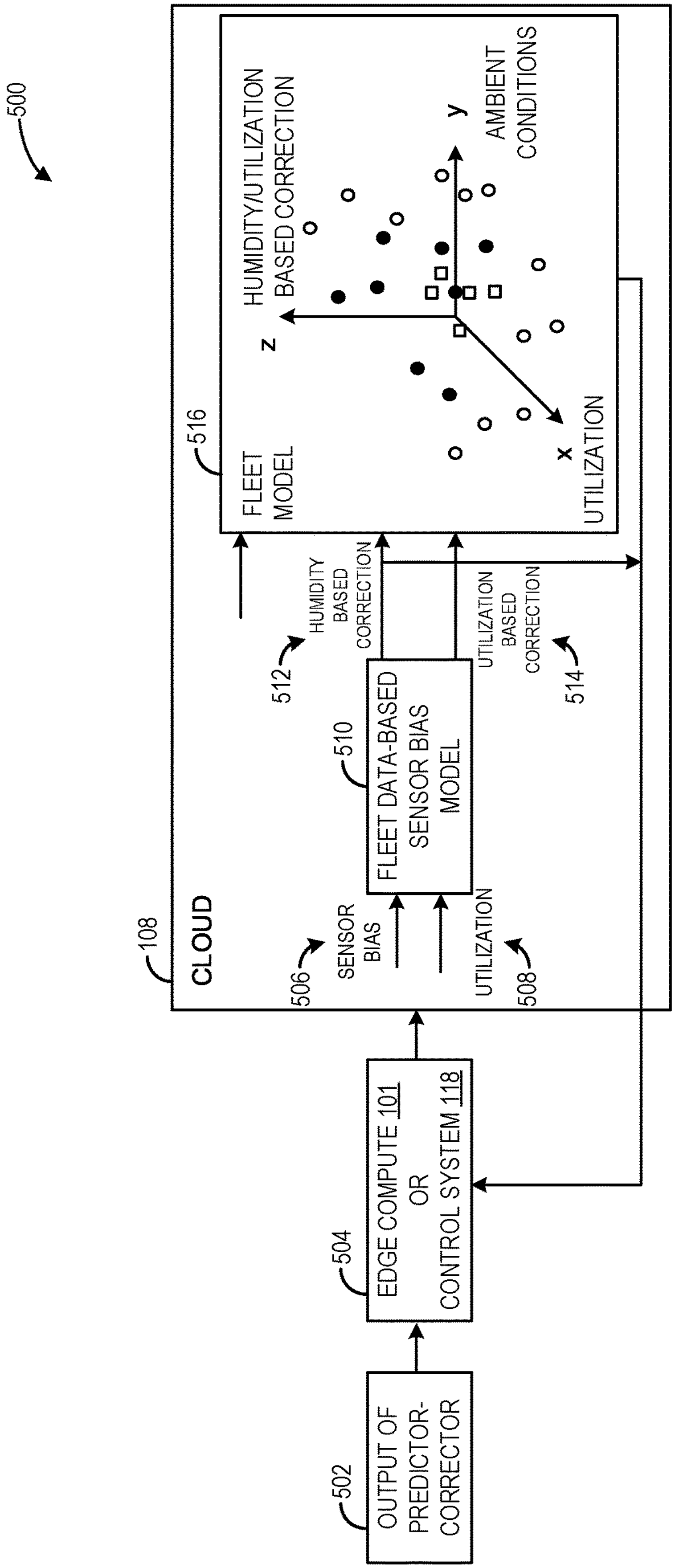
FIG. 5 illustrates an example edge-cloud architecture for sensor bias prediction based on ambient conditions, utilization levels, and a fleet model tracked over time.
Figure 6:
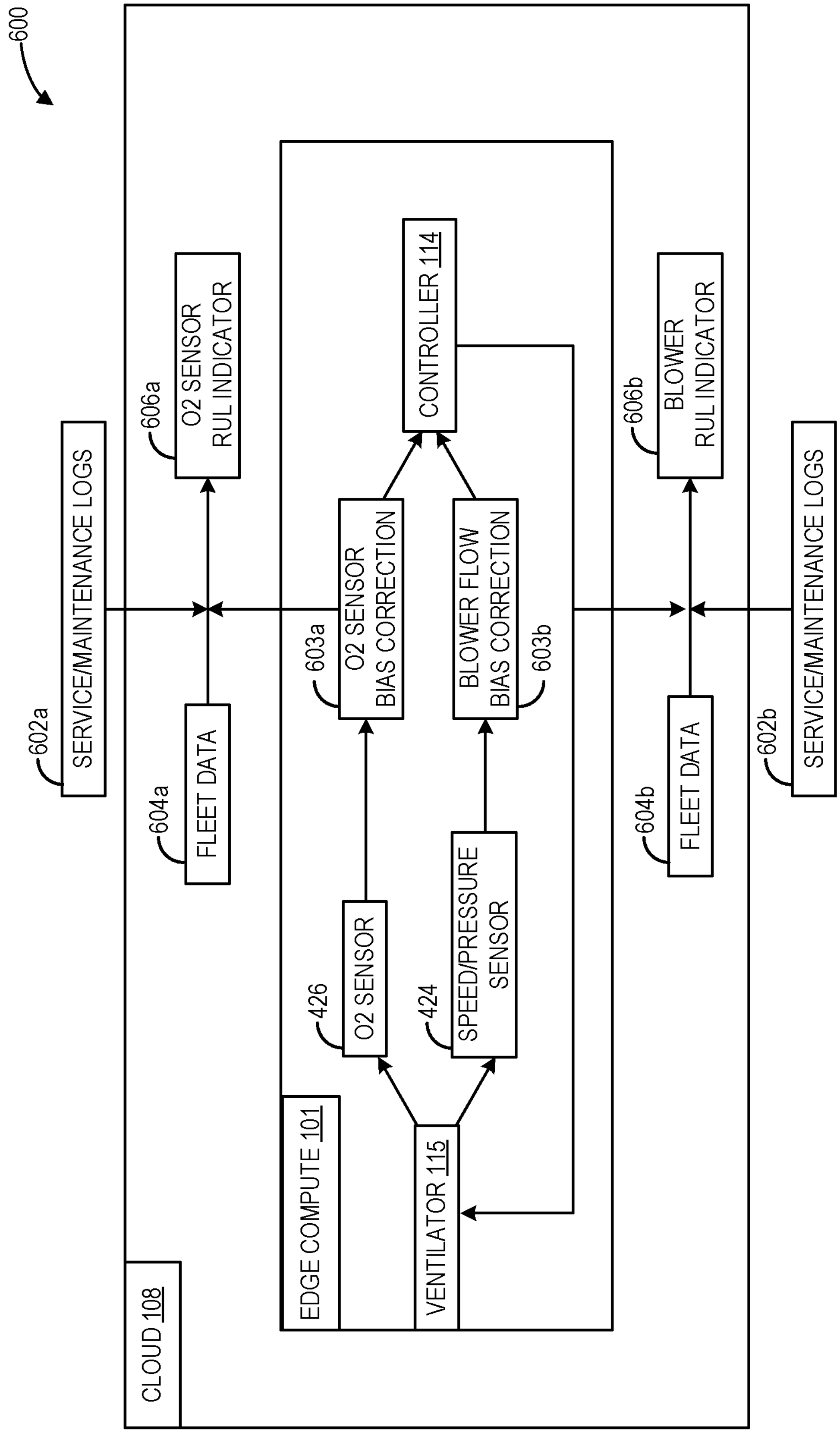
FIG. 6 illustrates an example of condition-based maintenance for a fleet of ventilators, based on the edge-cloud architecture described in FIG. 5.

The following description relates to various embodiments of methods and systems for predicting a reliability of a mechanical ventilator of a ventilator system. One such ventilator system employing a reliability prediction method is illustrated in FIG. 1, including an adaptable ventilator model and a plurality of on-premises and cloud-based functionalities supporting the management of the mechanical ventilator. The method may include a state machine controlling operation of the ventilator tracking the reliability of the ventilator through predictor corrector architecture, an example of which is shown in FIG. 2. An exemplary illustration of a reliability prediction based on a predicted bias of a sensor and a sensor fault is given in FIG. 3. An example mechanical ventilator pneumatic architecture for which an adaptable ventilator model and state machine controlling operation may be developed is illustrated in FIG. 4. A mechanical ventilator in communication with a supervisory system using edge-cloud architecture to track sensor bias over time and utilization is illustrated in FIG. 5. An example condition-based maintenance for a fleet of ventilators based on tracking the reliability predicted for each ventilator in the fleet over time is shown in FIG. 6. As a result of the systems and methods described herein, an ease of use of the ventilator system may be increased, mechanical ventilator maintenance may be made more efficient, and a likelihood of patient discomfort may be reduced.

Embodiments of the present disclosure will now be described, by way of example, with reference to the figures, in which FIG. 1 illustrates a block diagram of a system 100. In the illustrated embodiment, the system 100 is a mechanical ventilator system for a mechanical ventilator 115. Mechanical ventilator 115 is connected to components to detect and display reliability predictions in the system 100.

Mechanical ventilator 115 may take in inputs from an operator (e.g., doctor, nurse), such as parameters for erroneous value detection, thresholds for sensor and/or actuator bias, and the like. Mechanical ventilator 115 may be connected to a ventilator model 102, where input from operators into mechanical ventilator 115 may also be input into ventilator model 102 as parameters for calculations the ventilator model 102 performs. Mechanical ventilator 115 may be connected to a predictor-corrector 116, where input from operators into mechanical ventilator 115 may also be input into predictor-corrector 116 as well as readings from mechanical ventilator 115 such as oxygen levels, positive end-expiratory pressure (PEEP), and the like. Mechanical ventilator 115 may also be connected to a ventilator supervisory control system 118, where any readings from mechanical ventilator 115 may be input into ventilator supervisory control system 118 for monitoring and correcting any potential error detected in the components of mechanical ventilator 115.

In some embodiments, the operator may additionally or alternatively control one or more operating parameters of mechanical ventilator 115 via an electronic controller 114 of mechanical ventilator 115. Controller 114 includes a processor operatively connected to a memory. The memory may be a non-transitory computer-readable medium and may be configured to store computer executable code (e.g., instructions) to be processed by the processor in order to execute one or more routines, such as those described herein. The memory may also be configured to store data received by the processor. Controller 114 may be communicatively coupled (e.g., via wired or wireless connections) to one or more external or remote computing devices, such as a hospital computing system, and may be configured to send and receive various information, such as electronic medical record information, procedure information, and so forth. Controller 114 may also be electronically coupled to various other components of mechanical ventilator 115.

Controller 114 receives signals from the various sensors of mechanical ventilator 115 and employs the various actuators of mechanical ventilator 115 to adjust operation of mechanical ventilator 115 based on received signals and instructions stored on the memory of controller 114. For example, the flow of gases to an inspiratory port may be controlled via an input device (e.g., keyboard, touchscreen, etc.) coupled to the electronic controller of mechanical ventilator 115. Controller 114 may display operating parameters of mechanical ventilator 115 via a GUI display of a ventilator interface 120. Controller 114 may receive signals (e.g., electrical signals) via the input device and may adjust operating parameters of mechanical ventilator 115 in response (e.g., responsive) to the received signals.

As one example, the operator may input a desired concentration of an anesthetic agent to be delivered to the patient. A corresponding valve position of one or more valves of the mechanical ventilator (e.g., a position of one or more bypass valves) may be empirically determined and stored in a predetermined lookup table or function in a memory of the controller. For example, the controller may receive the desired concentration of the anesthetic agent via the input device and may determine an amount of opening of the one or more valves corresponding to the desired concentration of the anesthetic agent based on the lookup table, with the input being the concentration of the anesthetic agent and the output being the valve position of the one or more valves. The controller may transmit an electrical signal to an actuator of the one or more valves in order to adjust each of the one or more valves to the corresponding output valve position. In some examples, the controller may compare the desired flow rate of gases to a measured flow rate of gases, such as measured by an inspiratory flow sensor, for example.

Controller 114 is shown in FIG. 1 for illustrative purposes, and it is to be understood that controller 114 may be located in various locations within, around, and/or remote from mechanical ventilator 115. As an example, controller 114 may include multiple devices/modules that may be distributed throughout mechanical ventilator 115. As such, controller 114 may include a plurality of controllers at various locations within mechanical ventilator 115. As another example, additionally or alternatively, controller 114 may include one or more devices/modules that are external to mechanical ventilator 115, located proximate to (e.g., in a same room) or remote from (e.g., a remote server) mechanical ventilator 115. In each example, the multiple devices/modules may be communicatively coupled through wired and/or wireless connections.

Ventilator model 102 may be a semi-empirical physics-based model running in real-time on a processor, e.g., of controller 114, to estimate a current state of sensors and/or actuators of mechanical ventilator 115. In one example, ventilator model 102 may use multi-dimensional linearized equations built from mass, energy and momentum balance equations with parameters and linearization done in real-time through machine learning methods. Ventilator model 102 may generate an estimate of sensor and/or actuator functioning using information obtained from components of mechanical ventilator 115, e.g., high-pressure channel, blower speed, pressure post-blower values. Ventilator model 102 may be embedded on ventilator system 100 or in proximity to ventilator system 100 through a compute module. In some examples, inputs to the model may be obtained from mechanical ventilator 115 or through a bi-directional cloud connection to cloud network 108. Ventilator model 102 may be connected to predictor-corrector 116, where one or more estimates calculated by ventilator model 102, such as oxygen level estimates, PEEP estimates, error threshold estimates, and the like, may be input into predictor-corrector 116. Ventilator model 102 may also be connected to an edge compute box 101, where one or more calculations performed by ventilator model 102 may be input to edge compute box 101 so a performance of ventilator model 102 may be evaluated. In one example, edge compute box 101 may be an edge processor.

Edge compute box 101 may have a bi-directional cloud connection to cloud network 108, where any diagnostics from mechanical ventilator 115, ventilator supervisory control system 118, and ventilator model 102 may be input into cloud network 108 to be aggregated with data from other ventilator systems via cloud network 108. Cloud network 108 may input error thresholds and other parameters for ventilator component readings into edge compute box 101, such that edge compute box 101 may communicate with other components in ventilator system 100 given the data shared via the bi-directional cloud connection. Edge compute box 101 may be connected to ventilator supervisory control system 118, where any error thresholds from cloud network 108 may be input into ventilator supervisory control system 118, and any diagnostics from ventilator supervisory control system 118 may be input into edge compute box 101 communicated via the bi-directional cloud connection to the cloud network 108.

Cloud network 108 may include mechanical ventilator fleet data from a plurality of mechanical ventilators that may include readings given a plurality of conditions, such as ambient environments, utilization techniques, and the like. Cloud network 108 may further include a plurality of fleet models to facilitate sensor bias calculations performed by the system to detect local sensor biases. The plurality of fleet models may be considered fleet data-based sensor bias models, where each fleet model may differentiate bias accumulation due to ambient conditions of the ventilator (e.g., changes in humidity) or utilization (e.g., misuse due to inexperience). Tracking ventilator utilization over time, such as how biases may accumulate, may help classify a reliability of local sensors for the fleet of ventilators. The plurality of fleet models may separate bias corrections from ambient conditions and/or utilization, and may communicate fault thresholds and operation modes based on fault thresholds to edge compute box 101. In this way, the plurality of fleet models may account for and classify changes in data from sensors and/or actuators of mechanical ventilators due to ambient conditions and/or utilization separately from changes in data from sensors and/or actuators of mechanical ventilators due to corrections performed by the system or the operator. Fleet bias accumulation data classified by ambient condition and utilization may be deployed to edge compute box 101 for adapting ventilator model 102 to improve reliability of sensors and other components of the ventilators of the fleet. The plurality of fleet models may indicate any ventilators connected to the fleet, which are approaching a fault (e.g., conditions leading to patient discomfort) based on ambient conditions and/or utilization, meaning that the ventilators approaching the fault may enter a fault-tolerant operational mode to accommodate any potential faults that may occur. A ventilator may be considered to be approaching a fault based on conditions such as an increase in frequency of times an absolute value of difference between data from sensors and/or actuators of the ventilator and a fault threshold is less than a predetermined amount. The plurality of fleet models may differentiate ventilators connected to the fleet based on a closeness to triggering a fault, where ventilators closer to triggering a fault may be classified differently from ventilators that may be new or ventilators that may not be close to triggering a fault. In this way, cloud network 108 may help determine a state of health of the ventilator using the plurality of fleet models based on ambient conditions, and may increase an efficiency of any servicing that may occur to a ventilator as a result of determining the state of health of the ventilator using the plurality of fleet models.

Predictor-corrector 116 may compare real-time sensed outputs from mechanical ventilator 115, such as oxygen levels and/or PEEP levels, to outputs of the ventilator model 102, e.g., prediction estimates, to determine a predicted bias that may be present in the readings from mechanical ventilator 115 due to component error. Predictor-corrector 116 may be connected to a ventilator interface 120, where the readings from mechanical ventilator 115 may be input into ventilator interface 120 as well as estimates from ventilator model 102 to be displayed. Real-time determinations made by predictor-corrector 116 may be displayed on the GUI of the ventilator interface 120. Predictor-corrector 116 may be connected to ventilator supervisory control system 118. In one example, output of the predictor-corrector 116, e.g., comparisons or filtered readings based on a difference between readings from mechanical ventilator 115 and estimates from ventilator model 102, may be monitored by the ventilator supervisor control system 118. Ventilator supervisory control system 118 may communicate with mechanical ventilator 115 and edge compute box 101. In some examples, ventilator supervisory control system 118 may provide input to edge compute box 101 for potentially adapting ventilator model 102 and communicating with cloud network 108.

Ventilator interface 120 may display on the GUI sensor readings from mechanical ventilator 115 as well as estimates from ventilator model 102. In one example, a warning indication, e.g., alerts, based on a discrepancy in sensor values exceeding an error threshold may be displayed to the operator, prompting any potential operator-based corrections and/or calibrations to components of the mechanical ventilator. In one example, ventilator interface 120 may display oxygen levels, PEEP levels, or other parameters indicative of patient comfort, e.g., patient comfort index.

FIG. 2 shows a state diagram illustrating an example state machine 200 for tracking a predicted reliability in a mechanical ventilator, such as mechanical ventilator 115 of FIG. 1. The state machine may use a ventilator supervisory control system, such as ventilator supervisory control system 118 of FIG. 1, a ventilator model, such as ventilator model 102 of FIG. 1, and signals from sensors and/or actuators of the mechanical ventilator, such as those described below in FIG. 4. The ventilator supervisory control system may receive fault thresholds locally or from a cloud network, such as cloud network 108 of FIG. 1. In one example, reliability predictions of the mechanical ventilator during operation may be compared to fault thresholds such that if any reliability prediction of the mechanical ventilator crosses an associated fault threshold, the mechanical ventilator may transition from one state to another. Reliability predictions may include discrepancies indicative of sensor biases, actuator biases, gas leaks, and the like as a result of a plurality of factors including but not limited to component age and/or degradation, improper utilization, and variations in environmental conditions. In an example, upon detection of a discrepancy, the mechanical ventilator may transition to a bias state or a degradation state, where the ventilator supervisory control system may operate with a warning indicating degradation. In another example, the ventilator supervisory control system may make adjustments to the ventilator operations based on a comparison of observed data to expected data supplied from the ventilator model and one or more thresholds. In a further example, the ventilator supervisory control system may generate actions for the operator, such as adjustments to the operation of the mechanical ventilator. In some examples, limited ventilator operation may be enabled to continue in the degraded operation state even with detected faults by including corrections to enable fault tolerance. When a more severe discrepancy is detected, the ventilator may enter a shutdown state, based on crossing one or more high severity fault thresholds. In some examples, a shutdown state may include deactivated ventilator operation. In an example, an operator may be notified when a fault is detected by having a notification presented on a GUI display, allowing the operator to manually adjust operating parameters to correct a fault when the mechanical ventilator enters a bias state and/or a degradation state.

The mechanical ventilator may be considered to be operating in a normal operation state when the mechanical ventilator is operating with standard operating parameters, herein referred to as normal mode 201. The normal mode 201 may include all standard and typical behaviors of the mechanical ventilator, such as supplying predetermined amounts of oxygen to a patient, measuring oxygen levels in the mechanical ventilator via an oxygen sensor, regulating pressure of supplied oxygen to the patient, filtering supplied oxygen to the patient, measuring pressure levels in the mechanical ventilator via a pressure sensor, filtering bacteria during inhalation and exhalation of the patient, and the like. Normal operation state parameters that may be included in the normal mode 201 may be predetermined by the ventilator supervisory control system and the operator may verify the normal operation state parameters included in the normal mode 201. During operation, data supplied by sensors and actuators in the mechanical ventilator may be displayed on the associated GUI display, such as ventilator interface 120 of FIG. 1.

The predicted reliability of the mechanical ventilator may transition from the normal mode 201 to a pressure bias state, herein referred to as pressure bias mode 204, based on a detected pressure bias by the system, represented by arrow 202. The detected pressure bias may be due to a frequent change in ambient conditions (e.g., humidity), and pressure sensors included in the mechanical ventilator may show biases in sensor readings. In one example, pressure may be measured using air flow sensors that may be configured within the mechanical ventilator. The airflow sensors may include a thin, flexible metal reed that is coupled perpendicular to an air flow path of the air flow sensor. The reed deflects proportionally to airflow through the airflow path, and a pressure across the reed (e.g., determined based on pressures measured upstream and downstream of the reed) may be used to determine a flow rate of the airflow. For example, the airflow sensor may be calibrated during manufacturing to determine a relationship between the pressure across the reed and the flow rate, which may be referenced to determine the flow rate of the airflow during use of the mechanical ventilator. However, the relationship may change over time due to metal fatigue of the reed and other sources of calibration drift. Therefore, an accuracy of the flow rate determined based on the pressure across the reed may change over time. Biases in pressure, through either pressure sensors or airflow sensors, may be detected as a result of a predictor-corrector, such as the predictor-corrector 116 of FIG. 1, and a predictor-corrector architecture comparing a pressure measurement from the sensors to an estimated pressure measurement from the ventilator model. The predictor-corrector may output the comparison of the two measurements to an edge compute box, such as the edge compute box 101 of FIG. 1, where the comparison of the pressure measurement from the sensors to the predicted pressure measurement may be input into a fleet model for pressure bias as a result of humidity to determine if the mechanical ventilator is approaching a fault or is at a fault. The mechanical ventilator may transition to the normal mode 201 if the fleet model(s) determines that the mechanical ventilator is not approaching a fault, and no additional generated actions may be taken to prevent patient discomfort, represented by arrow 203.

The mechanical ventilator may transition to a degraded operation state from the pressure bias mode 204, herein referred to as first fault mode 206, if a fault threshold set by fleet models in the cloud network is crossed, represented by arrow 205. Crossing a fault threshold may include an instance where a value normally greater than the fault threshold is now less than the fault threshold or an instance where a value normally less than the fault threshold is now greater than the fault threshold, where both instances may lead to patient discomfort. The mechanical ventilator may also transition to the first fault mode 206 if the fleet model(s) determines that the mechanical ventilator is approaching a fault while in the pressure bias mode 204, as a preventative action to prevent possible future patient discomfort. The first fault mode 206 may indicate to the operator on the GUI display that the first fault mode 206 is active, and may further include displaying model outputs to the operator relating to the fault that is associated with the first fault mode 206 as well as readings from any sensors relating to the fault so the operator may make a corresponding correction to offset the reliability and prevent patient discomfort. The operator may monitor sensor measurements and component behavior while the mechanical ventilator is in first fault mode 206, and the operator may determine when the mechanical ventilator may transition to the normal mode 201. In one example, a prompt may be presented to the operator on the GUI display to allow the operator to indicate when the mechanical ventilator may transition to the normal mode 201.

The mechanical ventilator may transition from the normal mode 201 to an actuator bias state, herein referred to actuator bias mode 209, based on a detected actuator bias by the system, represented by arrow 207. The detected actuator bias may be due to a plurality of conditions, including but not limited to an amount of changes in flow rate throughout the mechanical ventilator, component degradation, or improper utilization. In one example, a controller, such as controller 114 of FIG. 1, may transmit an electrical signal to an actuator of one or more valves in the mechanical ventilator in order to adjust each of the one or more valves to a corresponding output valve position, and component degradation may cause a difference in an instructed output valve position and an actual output valve position, which may lead to a detection of actuator bias. In some examples, the controller may compare a desired flow rate of gases to a measured flow rate of gases, such as measured by an inspiratory flow sensor, and if an absolute value of difference between the desired flow rate of gases to the measured flow rate of gases exceeds a threshold amount within a threshold duration of time, actuator bias may be detected. In one example, actuator bias may be determined using airflow sensors configured within the mechanical ventilator, as described above. The airflow sensor calibration at manufacture may change over the lifetime use of the ventilator due to metal fatigue of the reed and other sources of calibration drift. Therefore, an accuracy of the flow rate determined based on the pressure across the reed may change over time. Actuator biases may be detected as a result of the controller using a lookup table to compare known values of expected pressure and flow speed given an expected input voltage against actual values of pressure and flow speed given an actual input voltage. Biases in flow rates, through either pressure sensors or air flow sensors, may be detected as a result of the predictor-corrector architecture comparing an air flow measurement from the sensors to an estimated air flow measurement from the ventilator model. The predictor-corrector may output the comparison of the two measurements to the edge compute box, where the comparison of the air flow measurement from the sensors to the predicted air flow measurement may be input into a fleet model for actuator bias as a result of air flow to determine if the mechanical ventilator is approaching or is at a fault. The mechanical ventilator may transition to the normal mode 201 if the fleet model(s) determines that the mechanical ventilator is not approaching a fault, and no generated actions may be taken to prevent patient discomfort, represented by arrow 208. In one example, the lookup table used to detect actuator bias may be recalibrated with new values and/or ranges of values based on a current instance of actuator bias detection to reduce a number of instances where the mechanical ventilator transitions from the actuator bias mode 209 to the normal mode 201 due to an inaccurate actuator bias detection.

The mechanical ventilator may transition to a second degraded state, herein referred to as a second fault mode 211, from the actuator bias mode 209 if a fault threshold set by fleet models in the cloud network is crossed, represented by arrow 210. Crossing a fault threshold may include an instance where a value normally greater than the fault threshold is now less than the fault threshold or an instance where a value normally less than the fault threshold is now greater than the fault threshold, where both instances may lead to patient discomfort. The mechanical ventilator may also transition to the second fault mode 211 if the fleet model(s) and/or lookup table determine that the mechanical ventilator is approaching a fault while in the actuator bias mode 209, as a preventative action to prevent possible future patient discomfort. The second fault mode 211 may indicate to the operator on the GUI display that the second fault mode 211 is active, and may further include displaying model outputs to the operator relating to the fault that is associated with the second fault mode 211 as well as readings from any sensors relating to the fault so the operator may make a corresponding correction to offset the reliability and prevent patient discomfort. The operator may monitor sensor measurements and component behavior while the mechanical ventilator is in second fault mode 211, and the operator may determine when the mechanical ventilator may transition to the normal mode 201. In one example, a prompt may be presented to the operator on the GUI display to allow the operator to indicate when the mechanical ventilator may transition to the normal mode 201.

The mechanical ventilator may transition from the normal mode 201 to an oxygen estimation state, herein referred to as oxygen estimation mode 214, based on a detected amount of oxygen by the mechanical ventilator, represented by arrow 212. The detected amount of oxygen by the mechanical ventilator may be outside of a range of values representing expected amounts of oxygen by the mechanical ventilator, transitioning the mechanical ventilator to the oxygen estimation mode 214. The detected amount of oxygen by the mechanical ventilator may be outside of the range of values for expected amounts of oxygen due to scenarios where the mechanical ventilator may be operating in less-controlled environments, e.g., where humidity variations may be high and interfere with oxygen probe functionality. Inaccurate oxygen measurements may be detected as a result of the predictor corrector architecture comparing an oxygen measurement from the sensors to an estimated oxygen measurement from the ventilator model. The predictor-corrector may output the comparison of the two measurements to the edge compute box where the comparison of the oxygen measurement from the sensors to the predicted oxygen measurement may be input to a fleet model for oxygen bias as a result of utilization to determine if the mechanical ventilator is approaching or is at a fault. The mechanical ventilator may transition to the normal mode 201 if the fleet model(s) determines that the mechanical ventilator is not approaching a fault, and no generated actions may be taken to prevent patient discomfort, represented by arrow 213.

If an amount of oxygen is detected outside an oxygen first threshold, the mechanical ventilator may transition from the oxygen estimation mode 214 to an oxygen backup state, herein referred to as oxygen backup mode 217, represented by arrow 215. In the oxygen backup mode, an oxygen sensor fault may be detected as a result of the predictor-corrector architecture comparing an oxygen measurement from the sensors to an estimated oxygen measurement from the ventilator model. The predictor-corrector may output the comparison of the two measurements to the edge compute box where the comparison of the oxygen measurement from the sensors to the predicted oxygen measurement may be input into a fleet model for oxygen bias as a result of utilization to determine if the mechanical ventilator is approaching or is at a second fault. In one example, the oxygen backup state may be considered a discrepancy of higher severity due to sensor reliability.

If an oxygen supply is detected outside a higher severity threshold, the mechanical ventilator may transition from the oxygen backup mode 217 to a shutdown state, herein referred to as a third fault mode 219, represented by arrow 218. Crossing a higher severity oxygen threshold may include an instance where a value normally greater than the threshold is now less than the threshold or an instance where a value normally less than the threshold is now greater than the threshold, where both instances may lead to patient discomfort. The mechanical ventilator may also transition to the third fault mode 219 if the fleet model(s) and/or lookup table determines that the mechanical ventilator is approaching a fault while in the oxygen backup mode 217, as a preventative action to prevent possible future patient discomfort. The mechanical ventilator may also transition to the third fault mode from the normal mode 201, represented by arrow 216. The third fault mode 219 may indicate to the operator on the GUI display that the third fault mode 219 is active, and may further include diagnostics relating to a fault that is associated with the third fault mode 219 as well as instructions to use a different mechanical ventilator. In one example, instructions for the mechanical ventilator in third fault mode 219 may include deactivating ventilator operation until maintenance is performed. In another example, the operator may monitor sensor measurements and component behavior while the mechanical ventilator is in the third fault mode and the operator may determine when the mechanical ventilator may transition to the normal mode 201. In one example, a prompt may be presented to the operator on the GUI display to allow the operator to indicate when the mechanical ventilator may transition to the normal mode 201.

The mechanical ventilator may transition from the normal mode 201 to a gas leak state, herein referred to as gas leak mode 221, based on a detected amount of gas leakage in the ventilator tubes, represented by arrow 220. In one example, gas leakage may include a leakage of oxygen gas. The detected amount of gas leakage in the ventilator tubes may be outside of a range of values representing expected amounts of gas leakage, transitioning the mechanical ventilator to the gas leak mode 221. The detected amount of gas leakage may be outside of the range of values for expected amounts of gas leakage due to conditions such as degradation or improper utilization of components in the flow path, e.g., valves, pressure regulators, flow restrictors. In one example, a controller may transmit an electrical signal to an actuator of one or more valves in the mechanical ventilator in order to adjust each of the one or more valves to a corresponding output valve position, and component degradation may cause a difference in an instructed output valve position and an actual output valve position, which may lead to gas leakage. In some examples, the controller may compare a desired gas pressure to a measured gas pressure, such as measured by an inspiratory gas pressure sensor, and if an absolute value of difference between the desired pressure to the measured pressure of gases falls outside a threshold amount within a threshold duration of time, gas leakage may be detected. Gas leakage may be detected as a result of the controller using a lookup table to compare known values of expected pressure given an expected valve adjustment against actual values of pressure and flow speed given an actual valve adjustment. Gas leakage passing pressure sensors or other sensors, e.g., air flow, may be detected as a result of the predictor corrector architecture comparing a gas pressure measurement from the sensors to an estimated pressure measurement from the ventilator model. The predictor-corrector may output the comparison of the two measurements to the edge compute box, where the comparison of the gas pressure measurement from the sensors to the predicted gas pressure measurement may be input into a fleet model for gas leakage as a result of gas pressure to determine if the mechanical ventilator is approaching or is at a fault. In one example, the gas leak mode 221 may be considered a degraded operation state and a higher severity fault type, such that, the mechanical ventilator may remain in the gas leak mode briefly. In gas leak mode, the mechanical ventilator may increase gas intake effort to compensate for the leakage and to prevent patient discomfort. In one example, the lookup table used to detect gas leakage may be recalibrated with new values and/or ranges of values based on a current instance of gas leakage detection to estimate an amount of gas pressure to increase to maintain appropriate gas flow.

From gas leak mode, the mechanical ventilator may transition to a shutdown state, herein referred to as a fourth fault mode 223, represented by arrow 222. The fourth fault mode 223 may indicate to the operator on the GUI display that the fourth fault mode 223 is active, and may further include diagnostics relating to a fault that is associated with the fourth fault mode 223 as well as instructions to use a different mechanical ventilator. In one example, instructions for the mechanical ventilator in fourth fault mode 223 may include deactivating ventilator operation until maintenance is performed. In another example, the operator may monitor sensor measurements and component behavior while the mechanical ventilator is in the fourth fault mode and the operator may determine when the mechanical ventilator may transition to the normal mode 201. In one example, a prompt may be presented to the operator on the GUI display to allow the operator to indicate when the mechanical ventilator may transition to the normal mode 201.

Figure 3:
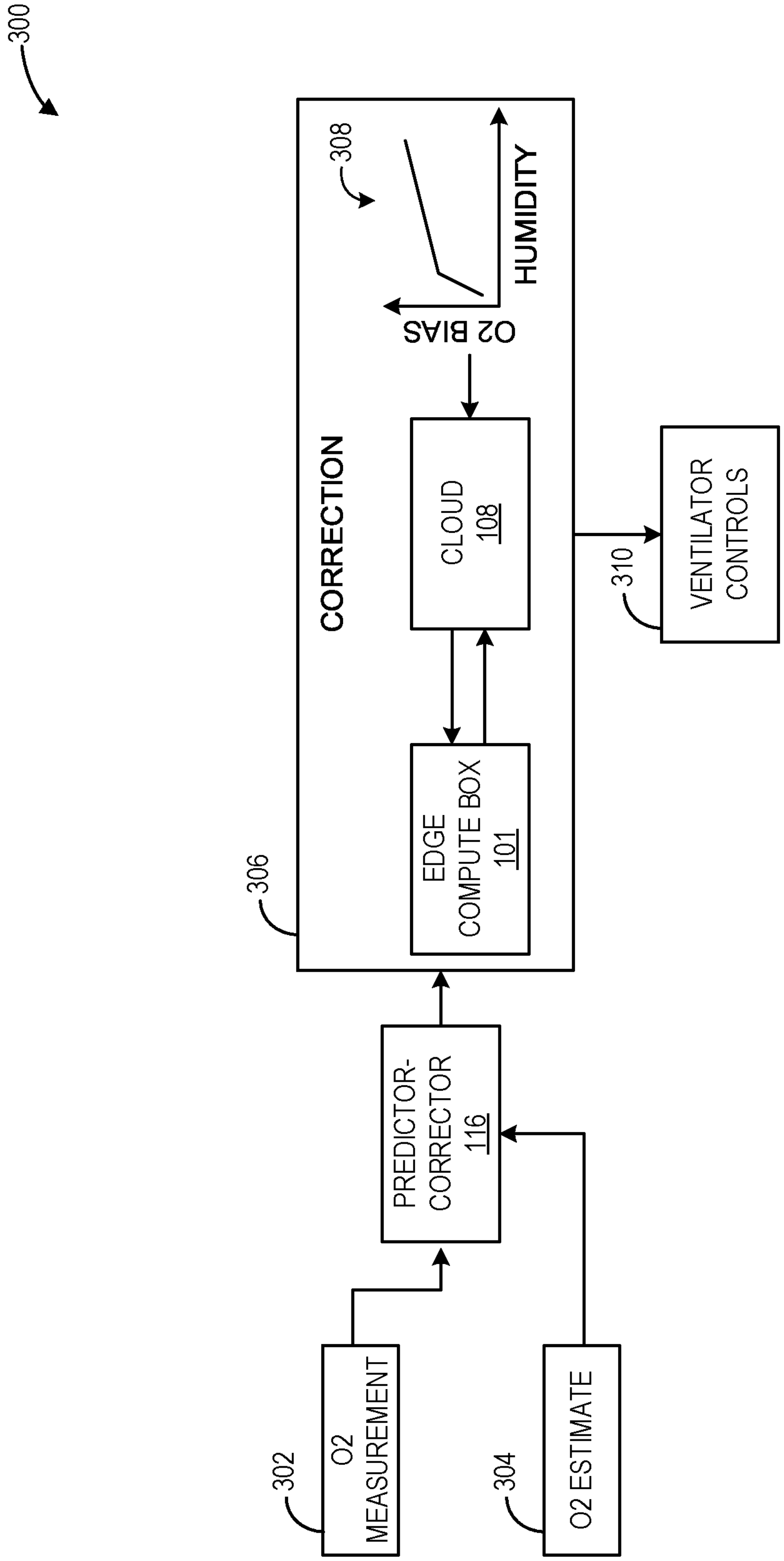
FIG. 3 illustrates a schematic diagram of an example predictor-corrector operation based on a ventilator model and sensor signals.

Turning now to FIG. 3, a schematic diagram 300 illustrating an example method for reliability prediction and correction in a ventilator system is shown. In the example, a bias state is detected based on a discrepancy between a modeled ventilator parameter and a sensed ventilator parameter, indicating a change in the reliability for a sensor of a mechanical ventilator, such as described with reference to state machine 200 of FIG. 2. The bias state of the sensor is diagnosed and corrected using data aggregated for a plurality of mechanical ventilators connected in a cloud network. As described above with reference to FIG. 2, in some examples, a mechanical ventilator may operate in a less-controlled environment, e.g., during movement of a patient from an ICU to a surgical ward, where humidity variation is great. Moisture from the air may be absorbed into a sensor cable of an oxygen probe affecting the capacitance of the probe in measurement. The result of the moisture absorption may be an in-range or out-of-range fault for the sensor probe, in some examples. Oxygen bias may be diagnosed by comparing an actual oxygen level detected by one or more sensors of the mechanical ventilator to an oxygen estimate produced by a semi-empirical model. By analyzing oxygen sensor behavior as a function of various environmental conditions aggregated with data from other ventilator systems in a cloud network, the bias or creep from the one or more sensors may be diagnosed with respect to utilization and operating (e.g., ambient) conditions. The model outputs, such as information related to the reliability of the sensor, and instructions, such as a corresponding correction to offset the bias or creep, may be displayed on the ventilator interface.

Schematic diagram 300 includes an oxygen measurement 302. The oxygen measurement 302 is an example of a sensed ventilator parameter obtained from one or more sensors of the mechanical ventilator, such as those described below with reference to FIG. 4. One or more of the sensors of the mechanical ventilator may provide an oxygen measurement, e.g., an inspiratory flow and/or pressure sensor.

Schematic diagram 300 includes an oxygen estimate 304. The oxygen estimate 304 is an example of a modeled ventilator parameter estimated by a semi-empirical physics-based model. In one example, the model may be developed based on a digital model of a ventilator pneumatic architecture, such as the ventilator pneumatic architecture 400 described below with reference to FIG. 4. In one example, the model may use multi-dimensional linearized equations built from mass, energy and momentum balance equations with parameters and linearization done in real-time through machine learning methods. In one example, the semi-empirical physics-based model may estimate an expected oxygen flow rate from pressure, airflow, and/or other inputs including data obtained from an oxygen high-pressure channel, a blower speed, and a pressure post-blower value.

The oxygen measurement 302 and oxygen estimate 304 are input to a predictor-corrector, such as predictor-corrector 116 described in FIG. 1, for estimation of oxygen sensor bias using a pair of equations. The oxygen measurement 302 and oxygen estimate 304 are input to a random-walk model and a Kalman update. In one example, the random walk model may calculate as follows: $_{(k+1)}=x_k^{pred}$, where $x_k^{pred}$ and $x_k^{est}$ refer to the predicted and estimated bias using the model and sensor data at the $k^{th}$ instant, respectively. The Kalman update filters the model estimate as follows: $_{(k+1)}+_{(k+1)}^{pred}+K\cdot(z^{meas}-z^{pred})$ where the oxygen sensor measurement is $z^{meas}$ and the oxygen calculated from the physic-based model is $z^{pred}$. In an example, the output is an oxygen sensor bias measurement. In an example, an oxygen sensor bias measurement may be a time-averaged non-zero percent difference from the model estimate. In this example, the oxygen measurement 302 is detected at a quantity less than a preset non-zero oxygen threshold quantity.

A correction 306 of the oxygen sensor bias determined by the predictor-corrector may be computed by comparison to oxygen sensor bias data representative of a plurality of ventilators, e.g., a fleet of ventilators, aggregated in a cloud network, such as cloud network 108 of FIG. 1. Data representative of the fleet of ventilators e.g., fleet level data, may be accessed by the edge compute box 101 via the cloud network 108, and computed locally. Fleet level data may include ventilator behavioral information, e.g., sensor and/or actuator bias, with respect to various environmental and/or utilization conditions. In an example, the edge compute box 101 computes a fleet wide analytics algorithm to produce a plot 308 of oxygen bias as a function of humidity from the fleet data. The correction 306 may be deployed on-site by ventilator controls 310 of the mechanical ventilator to adjust a setting of the mechanical ventilator and reduce patient discomfort.

On analyzing the correlation of the oxygen sensor bias as a function of humidity, e.g., plot 308, the oxygen bias estimate of the example ventilator may be compared to an oxygen bias threshold to determine if the ventilator is approaching or is at a fault. In an example, the ventilator is transitioned to an oxygen estimation state, briefly. The knowledge-based representation computed during correction 306 may then be fed back into a supervisory control algorithm to correct oxygen dispensation in the ventilator, whereupon the ventilator may be transitioned to a normal state, as described with reference to the state machine 200 of FIG. 2.

An example pneumatic architecture of a mechanical ventilator 400 is described in more detail in FIG. 4. The mechanical ventilator 400 prepares a mixture of ambient and oxygen gases. The prepared gas mixture is pressurizingly passed through a series of lines intercepted by valves and filters. The filtered gas mixture flows out to a patient via breathing tubes. The mechanical ventilator 400 also includes a variety of sensors and actuators to monitor and adjust dispensation of the gas mixture. The mechanical ventilator 400 may be modeled by one or more semi-empirical physics-based models, such as ventilator model 102 of FIG. 1. The operation of the mechanical ventilator 400 may be monitored and controlled following the exemplary methods described herein.

The pneumatic architecture includes ambient air line 403, low pressure line 405, pre-mixture line 407, upper inhalation line 419*a*, lower inhalation line 419*b*, and exhalation line 443. A direction of gas flow is indicated by a plurality of arrows of the described lines. Ambient air 402 filters through standard inlet filter pair 404. After filtration, ambient air 402 enters mechanical ventilator 400 via ambient air line 403. Low-pressure (LP) oxygen 406 enters low pressure line 405 via port 409. In one example, LP oxygen 406 may flow at a rate less than 15 liters/minute (LPM). High-pressure (HP) oxygen 408 enters pre-mixture line 407 via port 411 passing through standard inlet filter 412, e.g., a 20 micron filter. In one example, HP oxygen may have a lower pressure threshold of 242 kilo Pascals (kPa) and an upper pressure threshold of 648 kPa.

After filtration, HP oxygen 408 continues through pressure regulator 414. In one example, pressure regulator 414 may restrict pressure to 30 pounds per square inch (PSI). Following filtering and regulating, HP oxygen 408 continues through rotameter 416 where the oxygen flow is further restricted. In one example, rotameter 416 may restrict HP oxygen 408 to 15 LPM. LP check valve 410 is located on low pressure line 405 downstream from port 409 for preventing back flow of HP oxygen. Low pressure line 405 fluidically couples to pre-mixture line 407 at rotameter 416. LP oxygen 406 enters pre-mixture line 407 via rotameter 416.

Ambient air line 403 fluidically couples to upper inhalation line 419*a* at mixing chamber 418. Ambient air 402, LP oxygen 406, and HP oxygen 408 combine in mixing chamber 418. In one example, mixing chamber 418 may have a 0.5 L capacity. A gas mixture exits mixing chamber 418 to enter upper inhalation line 419*a*. The gas mixture is received by blower 420, e.g., a turbine, operating at a fixed speed, e.g., 10 breaths/L. In one example, blower 420 may be operated by a mechanically coupled electric motor (not shown). The pressure of the gas mixture exiting the blower is regulated by flowing through proportional valve 422. In one example, proportional valve 422 is a voice coil-based proportional valve.

Multiple sensors measure gas pressure and oxygen along the flow path of upper inhalation line 419*a*. First pressure sensor 424 is downstream from blower 420 and proportional valve 422. In one example, first pressure sensor 424 measures a pressure of gas emitted from blower 420. Oxygen sensor 426 and check valve 428 thereafter are located along upper inhalation line 419*a*. Free breathing valve 430 is located along upper inhalation line 419*a* after check valve 428. Second pressure sensor 432 is downstream from free breathing valve 430.

Following the first pressure sensor 424 and before the oxygen sensor 426, the lower inhalation line 419*b* splits off from the upper inhalation line 419*a*. The lower inhalation line 419*b* fluidically couples to the upper inhalation line 419*a*. The lower inhalation line includes a bleed resister 436. A third pressure sensor 439 is adjacent to an outlet 441 of a pneumatic exhalation valve 438. Opposite the pressure sensor 439 is a disposable flow restrictor 437 of an opening to ambient air.

After second pressure sensor 432, the gas mixture flows via upper inhalation line 419*a* through a bacterial/viral filter 434 into inhalation breathing tube 442 wherefrom the pressurized gas mixture may be inspired by patient 446 via two-way breathing device 447. In one example, the ventilator 400 may be fitted with a 22 millimeter (mm) diameter inhalation breathing tube 442 for a male patient and a 15 mm diameter inhalation breathing tube 442 for a female patient.

Waste gas expirated by the patient 446 may be directed to exhalation breathing tube 444 via two-way breathing device 447. Waste gas is filtered through a bacterial/viral filter 440. Exhalation breathing tube 444 fluidically couples to exhalation line 443 following filter 440. Filtered exhalation flows through exhalation line 443 to pneumatic exhalation valve 438 to pass disposable flow restrictor 437 to the atmosphere. In one example, an exhaled gas pressure may be measured by pressure sensor 439 opposite the disposable flow restrictor.

In one example, one or more semi-empirical physics-based models, such as those employed in the methods described herein, may be developed for the ventilator pneumatic architecture 400 of FIG. 4. In one example, an oxygen model may be developed as follows. The oxygen concentration of gas in inhalation breathing tube 442 entering the patient lungs may be obtained through a numerical model, which calculates oxygen concentration from a pressure signal obtained from pressure sensor 424, blower flow 420, oxygen gas purity levels dispensed at 406, 408, gas inlet valve positions before 418, as well as environmental information of oxygen gas concentration. The numerical model may be further developed through gas flow-dynamics knowledge through mass balance along with initial tuning of hyperparameters in the model to adjust the signal levels based on the ventilator design.

Turning now to FIG. 5, a schematic diagram 500 illustrating a cloud-networked edge compute box operating as part of a supervisory system for a mechanical ventilator is shown. In the example, sensor and actuator reliability for a mechanical ventilator may be classified based on aggregate sensor bias data from plurality of fleet models. The plurality of fleet models may be considered a fleet data-based sensor bias model (e.g., fleet level data), where each fleet model may differentiate bias accumulation due to ambient conditions (e.g., changes in humidity) or utilization (e.g., misuse due to inexperience). In some examples, the fleet level data may differentiate bias accumulation due to ambient conditions or due to utilization to classify one or more ventilator component's reliability over time. In some examples, the fleet data-based sensor bias model may classify bias correction from ambient condition or utilization, and communicate the operational state and fault threshold back to the ventilator. Ventilator performance and ventilator life may be tracked over time based on the fleet level data, with operation and corrections made as needed, e.g., as described in state machine 200 of FIG. 2. In this way, fleet level data may determine the state of the ventilator health, informing patient care and ventilator maintenance, as needed.

A predictor-corrector output 502, such as a sensor bias estimate, may be input to a control component 504 of a ventilator system, such as the ventilator system 100 of FIG. 1. In one example, the control component 504 may be edge compute box 101 of FIG. 1. In another example, the control component 504 may be control system 118 of FIG. 1. The control component 504 may be on premises and in bidirectional communication with a cloud network, such as cloud network 108 of FIG. 1. The control component 504 may communicate low resolution data, e.g., data regarding an individual ventilator, via cloud network 108. In one example, low resolution data may include data from one or more sensors of the ventilator, such a sensor bias estimate 506. Additionally or alternatively, low resolution data may include control or diagnostic information related the ventilator, e.g., utilization 508.

In one example, fleet data-based sensor bias model 510 may track reliability of the sensor bias calculation for an individual ventilator against variations in environmental conditions or utilization, e.g., humidity, historical log data. Fleet data-based sensor bias model 510 may differentiate bias accumulation due to ambient conditions or utilization to classify sensor components' reliability at various stages of life. Humidity-based correction 512 and/or a utilization-based correction 514 may be determined for a ventilator based on fleet data-based sensor bias model 510. The output of fleet data-based sensor bias model 510, e.g., humidity and/or utilization corrections, may be visualized in a plot, such as fleet model plot 516. Fleet model plot 516 shows a status of individual ventilators located on a three dimensional plot of utilization (x-axis), ambient conditions (y-axis), and humidity- and/or utilization-based correction (x). Fleet model plot 516 shows hollow circles indicating the set of ventilators in the fleet that are on verge of fault based on environmental conditions and utilization. Hollow circle represent ventilators of the fleet will soon move towards a fault-tolerant operational mode. The hollow circles represent ventilators showing moderate levels of sensor and/or actuator bias and correction due to utilization and ambient condition variation. Fleet model plot 516 shows black circles indicating the fleet of ventilators, which are progressing towards fault. The black circles represent ventilators showing low to moderate levels of sensor and/or actuator bias and correction due to utilization and ambient condition variation. Hollow squares represent a new fleet of ventilators with low levels of use, minimal fluctuations in ambient conditions and minimal to no bias correction.

In one example, fleet data-based sensor bias model 510 may monitor and adjust the operation of a cloud-networked ventilator in response to varying environmental variations and utilization levels. A sensor bias calculation for a ventilator may be visualized in the context of other ventilators based on the fleet data-based sensor bias model, thus providing information about the reliability of the example ventilator. The fleet data-based sensor bias model can separate bias correction from ambient conditions, and utilization. Fleet data-based sensor bias model 516 may determine a ventilator operational state and/or fault thresholds for the ventilator, which may be transmitted back to control component 504 and used to adjust operation of the example ventilator. In this way, ventilator performance and ventilator life may be tracked over time based on fleet level data, streamlining operation protocols and/or maintenance, accordingly.

FIG. 6 illustrates a schematic diagram 600 of an example condition-based maintenance for tracking reliability predictions for a fleet of ventilators. In some examples, the methods disclosed herein may be performed on the existing compute footprint for the ventilators, including ventilators without cloud network capability, and thus involve minimal additional investment. In other examples, existing computational and connective capacity may be upgraded and/or modified. In some examples, establishing bidirectional cloud connectivity for a fleet of ventilators may enhance ventilator reliability predictions for enabling a smooth supply-chain flow of ventilator component replacement, substantially offsetting an upfront investment with downstream cost reduction related to fleet management.

The example illustrated in schematic diagram 600 includes components of the ventilator system 100 of FIG. 1. Ventilator 115 of FIG. 1 is shown. Ventilator 115 is in electronic communication with controller 114. Schematic diagram 600 includes ventilator 115 equipped with oxygen sensor 426 and first pressure sensor 424 of FIG. 4. Sensed ventilator parameters may be compared to modeled ventilator parameters, e.g., developed using ventilator model 102 of FIG. 1, with reliability predictions performed on-premises using the edge compute box 101. In one example, the ventilator 115, controller 114, and edge compute box 101 represent a single ventilator system among a fleet of cloud networked ventilator systems in cloud network 108. One or more reliability predictions for a ventilator system may be transmitted to the cloud network 108 and aggregated with one or more reliability predictions transmitted from plurality of ventilators. In one example, an oxygen sensor bias correction **603*a* may be determined for the oxygen sensor 426 and communicated to the controller 114 to adjust operation of the ventilator 115. In another example, a blower flow bias correction 603*b* may be determined for the first pressure sensor 424 and communicated to the controller 114 to adjust operation of the ventilator 115**. Sensor bias correction data, e.g., oxygen or pressure, for the ventilator system may be aggregated with data representing other ventilator systems in the cloud-networked fleet. The aggregated reliability predictions may be tracked over time and the ventilator modeled updated therefrom. In one example, the cloud network may include many ventilator systems distributed within one common care center, e.g., a single hospital location. In another example, the cloud network may include ventilator systems distributed over a larger geographic region including multiple common care center locations and the ventilator systems therein.

In FIG. 6, service/maintenance logs **602*a*, 602*b* may provide historical ventilator usage information about ventilator systems to the cloud network 108. Service/maintenance logs 602*a*, 602*b* may accompany and/or support fleet data 604*a*, 604*b*, which represent sensor data and actuator data, respectively. Within the cloud network, fleet data 604*a*, 604*b*, in combination with fleet service and/or maintenance logs 602*a*, 602*b*, may provide an indication of the remaining useful life (RUL) of sensors and/or actuators. In one example, an oxygen sensor RUL indicator 606*a* may be supported by fleet data 604*a* in combination with service and/or maintenance logs 602*a*. In another example, a blower RUL indicator 606*b* may be supported by fleet data 604*b* in combination with service and/or maintenance logs 602*b***.

As an example, a service and maintenance plan may be established based on the RUL indications for the fleet ventilators in the network. Maintenance may be scheduled for a set of ventilators based on a first RUL indication threshold. Replacement may be directed for a set of ventilators based on a second, shorter RUL indication threshold. In this way, cloud networking for fleet-level data provides an add-on value to enhance ventilator fault predictions for enabling a smooth supply-chain flow of ventilator maintenance and replacement.

In this way, a mechanical ventilator system may use a semi-empirical physics-based model to predict a reliability of a mechanical ventilator over time. Discrepancies between modeled parameters and sensor signals may be understood as a confidence metric indicating change in reliability of the sensor signals. By generating reliability predictions for sensors, actuators, and other components of the ventilator, and comparing the predictions against those of other ventilators, fault thresholds may be determined and ventilator operation adjusted accordingly. By establishing bidirectional communication with a fleet of cloud-networked ventilators, the model may adapt to real-time ambient condition and usage data to improve the reliability of individual ventilators and reduce reliance on redundant sensors. A technical effect of a fault-tolerant mechanical ventilator is more efficient ventilator maintenance, ease of service workflow to ensure serviceability, reduced downtime of ventilators, and reduced likelihood of patient discomfort.

The disclosure also provides support for a method, comprising: predicting a reliability of a ventilator during ventilator operation based on a discrepancy between a modeled ventilator parameter and a sensed ventilator parameter tracked over time and ventilator utilization. In a first example of the method, the method further comprises: displaying the predicted reliability to an operator of the ventilator, wherein the predicted reliability is based on a predicted bias of a sensor and a sensor fault. In a second example of the method, optionally including the first example, the method further comprises: transmitting the predicted reliability to a network aggregating predicted reliability transmitted from a plurality of ventilators. In a third example of the method, optionally including one or both of the first and second examples, the method further comprises: generating actions for the operator and displaying the generated actions to the operator. In a fourth example of the method, optionally including one or more or each of the first through third examples, the predicted reliability of the ventilator follows a state machine that includes states with limited ventilator operation enabled to continue even with detected faults by including corrections to enable fault tolerance, and that includes states with deactivated ventilator operation. In a fifth example of the method, optionally including one or more or each of the first through fourth examples, the modeled ventilator parameter is further based on a predictor corrector architecture, and where a severity of the discrepancy determines a state of the state machine. In a sixth example of the method, optionally including one or more or each of the first through fifth examples, the modeled ventilator parameter is based on a digital model embedded in the ventilator. In a seventh example of the method, optionally including one or more or each of the first through sixth examples, the method further comprises: the ventilator communicating with a supervisory system via a bi-directional cloud connection, the supervisory system tracking ventilator performance and ventilator life based on fleet level data of a fleet of ventilators including the ventilator, the fleet level data adjusting the ventilator for ambient conditions of the ventilator. In an eighth example of the method, optionally including one or more or each of the first through seventh examples, the method further comprises: displaying model outputs to an operator including information related to the reliability of the ventilator, and a corresponding correction to offset the reliability. In a ninth example of the method, optionally including one or more or each of the first through eighth examples, the fleet of ventilators includes ventilators within a common care center. In a tenth example of the method, optionally including one or more or each of the first through ninth examples, the method further comprises: generating condition-based maintenance for the fleet of ventilators based on tracking of the reliability predicted for each ventilator in the fleet over time.

The disclosure also provides support for a method, comprising: predicting a reliability of a ventilator during ventilator operation based on a discrepancy between a modeled ventilator parameter and a sensed ventilator parameter, the modeled ventilator parameter based on a digital model of the ventilator and sensor readings of the ventilator, and tracking the ventilator in a state machine, a state of the ventilator determined based on the predicted reliability, the state machine including a normal operation state, a degraded operation state where the ventilator continues to operate with a warning indicating degradation, and a shutdown state where the ventilator is not enabled to continue operation, and sending output of the digital model to an edge processor, the edge processor communicating with a supervisory control system monitoring the ventilator. In a first example of the method, the modeled ventilator parameter is further based on a predictor corrector architecture, and where a severity of the discrepancy determines a state of the ventilator. In a second example of the method, optionally including the first example, the degraded operation state includes an actuator bias state and an oxygen estimation fault state, and wherein the shutdown state includes a gas leak state.

The disclosure also provides support for a system, comprising: a mechanical ventilator, a ventilator model running in real-time on a processor, a predictor-corrector running in real-time on the processor receiving sensed outputs of the mechanical ventilator and an output of the ventilator model, a GUI generating a display, the display based on an output of the predictor-corrector, an edge processor, a ventilator supervisory control system running in real-time on a system, the ventilator supervisory control system receiving the output of the predictor-corrector, the ventilator supervisory control system communicating with the mechanical ventilator and the edge processor, the edge processor further communicating with the ventilator model and a cloud network. In a first example of the system, the mechanical ventilator includes a state machine controlling operation of the mechanical ventilator, the state machine including: a normal operation state, a pressure bias state, an oxygen estimation state, an oxygen backup state, and a gas leak state. In a second example of the system, optionally including the first example, a transition from the normal operation state to the pressure bias state is determined based on detection of a pressure bias by the system. In a third example of the system, optionally including one or both of the first and second examples, a transition from the normal operation state to the oxygen estimation state is determined based on detection of an oxygen bias by the system. In a fourth example of the system, optionally including one or more or each of the first through third examples, a transition from the oxygen estimation state to the oxygen backup state is determined based on detection of an oxygen bias outside a first threshold. In a fifth example of the system, optionally including one or more or each of the first through fourth examples, a transition from the normal operation state to the gas leak state is determined based on a detection of a gas leak by the system.

As used herein, the term “module” may include a hardware and/or software system that operates to perform one or more functions. For example, a module may include a computer processor, controller, or other logic-based device that performs operations based on instructions stored on a tangible and non-transitory computer readable storage medium, such as a computer memory. Alternatively, a module may include a hard-wired device that performs operations based on hard-wired logic of the device. Various modules shown in the attached figures may represent the hardware that operates based on software or hardwired instructions, the software that directs hardware to perform the operations, or a combination thereof.

"Modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:

a fleet of ventilators comprising a mechanical ventilator;

a cloud network comprising a plurality of fleet models for measuring conditions of the fleet of ventilators, wherein each of the plurality of fleet models is differentiated based on a closeness to triggering a fault, and each of the plurality of fleet models is configured to differentiate and determine a classification of a bias accumulation, due to ambient conditions or utilization of a corresponding mechanical ventilator of the fleet of ventilators that is modeled by the plurality of fleet models, by classifying a bias correction from varying ambient conditions or utilization of the corresponding mechanical ventilator, and adjusting operation of the corresponding mechanical ventilator, via the cloud network, in response to the bias correction;

a ventilator model of the mechanical ventilator running in real-time on a processor;

a predictor-corrector running in real-time on the processor, the predictor-corrector receiving outputs sensed by sensors of the mechanical ventilator, and an output of the ventilator model;

a GUI generating a display, the display based on an output of the predictor-corrector;

an edge processor; and a ventilator supervisory control system running in real-time on the system, the ventilator supervisory control system receiving the output of the predictor-corrector, the ventilator supervisory control system communicating with the mechanical ventilator and the edge processor, the edge processor further communicating with the ventilator model and the cloud network;

wherein the edge processor adjusts operation of the mechanical ventilator based on communication with the cloud network providing feedback related to other mechanical ventilators in a same fleet model of the plurality of fleet models with the mechanical ventilator.

2. The system of claim 1, wherein the classification of the bias accumulation due to ambient conditions or utilization is deployed to the edge processor for adapting the ventilator model, and the mechanical ventilator includes a state machine controlling operation of the mechanical ventilator, the state machine including:

a normal operation state;

a pressure bias state;

an oxygen estimation state;

an oxygen backup state;

and a gas leak state.

3. The system of claim 2, wherein a transition from the normal operation state to the pressure bias state is determined based on detection of a pressure bias by the system, wherein the ambient conditions include humidity.

4. The system of claim 2, wherein a transition from the normal operation state to the oxygen estimation state is determined based on detection of an oxygen bias by the system.

5. The system of claim 2, wherein a transition from the oxygen estimation state to the oxygen backup state is determined based on detection of an oxygen bias outside a first threshold.

6. The system of claim 2, wherein a transition from the normal operation state to the gas leak state is determined based on a detection of a gas leak by the system.

* * * * *